United States Patent [19]

Scott et al.

[11] 4,032,407

[45] June 28, 1977

[54] TAPERED BED BIOREACTOR

[75] Inventors: Charles D. Scott; Charles W. Hancher, both of Oak Ridge, Tenn.

[73] Assignee: The United States of America as represented by the United States Energy Research & Development Administration, Washington, D.C.

[22] Filed: Feb. 24, 1976

[21] Appl. No.: 660,902

[52] U.S. Cl. .............................. 195/127; 195/142; 195/116

[51] Int. Cl.² .......................................... C12B 1/00

[58] Field of Search ....... 195/127, 63, 68, DIG. 11, 195/139, 142, 143, 115; 23/284, 288 S

[56] References Cited

UNITED STATES PATENTS

| | | | |
|---|---|---|---|
| 2,980,731 | 4/1961 | Alheritiere et al. | 260/488 |
| 3,809,613 | 5/1974 | Vieth et al. | 195/63 |
| 3,928,143 | 12/1975 | Coughlin | 195/115 |
| 3,956,065 | 5/1976 | Idaszak et al. | 195/31 F |

OTHER PUBLICATIONS

*Chemical and Engineering News,* Aug. 18, 1975, pp. 22–41.

*Primary Examiner*—Lionel M. Shapiro
*Attorney, Agent, or Firm*—Dean E. Carlson; Stephen D. Hamel; John B. Hardaway

[57] ABSTRACT

A vertically oriented conically shaped column is used as a fluidized bed bioreactor wherein biologically catalyzed reactions are conducted in a continuous manner. The column utilizes a packing material a support having attached thereto a biologically active catalytic material.

7 Claims, 1 Drawing Figure

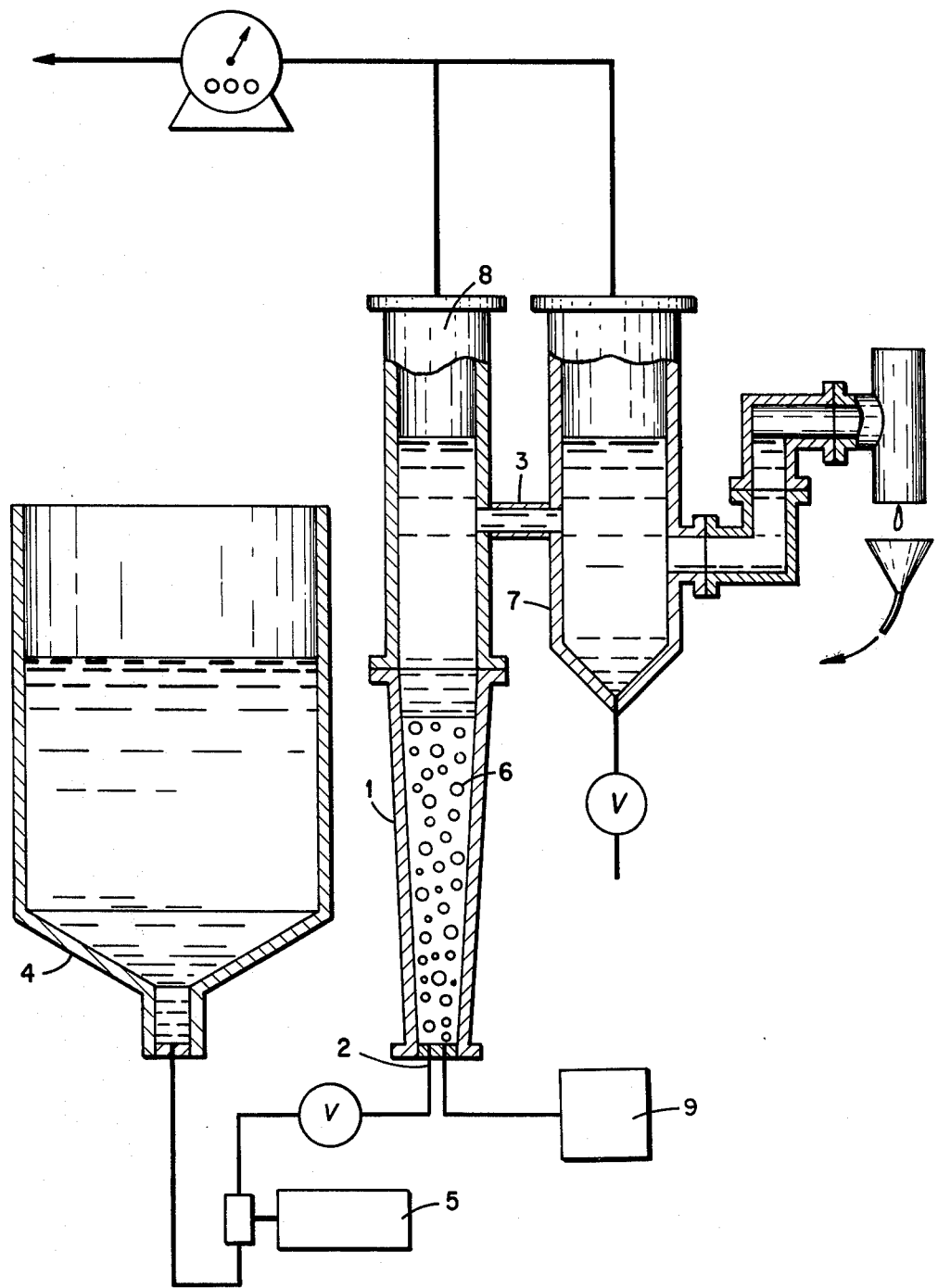

TAPERED BED BIOREACTOR

BACKGROUND OF THE INVENTION

This invention was made in the course of, or under, a contract with the Energy Research and Development Administration. It relates generally to the art of biologically catalyzed reactions and more particularly to an apparatus for carrying out such reactions.

Biological catalysts have been utilized for virtually the entire period of recorded history. Such catalysts comprise bacteria, yeasts, enzymes and algae. These biological catalysts have been used in various modes. Very few changes, however, have been made in techniques by which the biological catalysts are utilized. Most prior art processes have been carried out in the fermentation and sewage disposal arts. Such prior art processes are generally conducted in a batchwise manner. Attempts have been made to carry out such reactions in a continuous manner. Such attempts have culminated in the continuous stirred tank reactor and the packed bed reactor.

A continuous stirred tank reactor is a single stage reactor system where the solution concentration is the same throughout including the discharge concentrations. The reaction rates of most systems are directly dependent on the solution concentration. Therefore, a continuous stirred tank reactor must operate at the lower rate of discharge concentration regardless of feed concentration. The continuous stirring causes needed active biomass to be carried out with the discharge. This disadvantage can only be overcome by operating at a lower flow rate or installing a solid-liquid separator and recycling the needed active biomass. A packed bed reactor is an enclosed reactor containing submerged inert packing material which acts as a support for holding the biological catalyst. Most packed bed reactors are operated by directing the influent in an upward direction at a slow flow rate to promote separation of suspended solids from the effluent. Some packed bed reactors, however, are operated by directing the influent in a downward direction. A problem with the packed bed reactors is that the support material is frequently washed away with the effluent. Another problem of packed bed reactors is the build-up of biomass which occurs during continued use of the reactor. Biomass build-up results in column blockage and/or channeling such that the reactants no longer come in contact with the biological catalyst but continue through the reactor without being subjected to the catalytic activity of the biological catalyst.

A problem with any biological reactor is the death or denaturization of the biological catalyst. In such event, the reactor must be shut down and the packing material or support removed and replaced with a new support containing fresh biologically active catalytic material. In such situations the changeover can be quite costly and time consuming.

SUMMARY OF THE INVENTION

It is thus an object of this invention to provide a new apparatus for carrying out biologically catalyzed reactions.

It is a further object of this invention to provide an apparatus for carrying out biologically catalyzed reactions in a continuous manner and over a wide range of flow rates without destroying or losing the biological catalyst.

It is still a further object of this invention to provide such an apparatus which may be rapidly reactivated in the event of loss of biological activity.

These as well as other objects are accomplished by a tapered fluidized bed biological reactor having as the fluidized phase a support material to which is attached the biological catalyst and wherein the fluidizing medium is an aqueous phase containing the reactants.

BRIEF DESCRIPTION OF THE DRAWING

The single FIGURE of drawing illustrates in schematic form the apparatus in accordance with this invention.

DETAILED DESCRIPTION

In accordance with this invention it has been found that a tapered fluidized bed may be utilized as a bioreactor wherein the fluidized phase is a support material having attached or immobilized thereto a biological catalyst. The tapered fluidized bed may have as the biological catalyst a viable bacteria or yeast system or immobilized enzymes where the host is either self attached, chemically bonded or entrapped. Any of the prior art types of immobilized enzymatic systems may be utilized on a fluidizable support material within the reactor apparatus of this invention.

The apparatus of this invention may be best understood by referring to the single figure of drawing. The apparatus comprises a conically shaped column 1 having an inlet 2 and an outlet 3. The inlet 2 communicates with a source of reactants or reservoir 4. A variable flow rate pump 5 between the reactant source 4 and inlet 2 is provided for controlling the influent reactant flow rate. Column 1 is packed with a conventional support material 6 for the biologically active catalytic material which will be described with more particularity herein. Gaseous products are easily separated from the liquid phase by venting through exit 8. Gaseous reactants such as oxygen for use in aerobic reactions can be provided by gas introduction means 9. Alternatively, reservoir 4 may be provided with a means for providing a gaseous overpressure. The column 1 may have virtually any degree of taper for example, 0.25- 10° from the axis. It is preferred, however, that the column have a small taper so as to minimize eddys which would be created during the flow of reactants through the column. A taper of 0.5° to 2° from the axis of the column is preferred. If the cross sectional area of the inlet 2 is sufficiently small and the degree of taper is small, the flow profile throughout the reactor will have few large eddys and thus minimal backmixing. The taper allows a wide range of flow rates without loss of bed material since the fluidizing velocity decreases with reactor height, thus providing a bioreactor that can effectively operate with a variety of feed conditions. As the flow rate of the reactants within the aqueous phase of the fluidizing medium is gradually increased the bed progresses from a fixed bed to incipient fluidization and then to an expanded bed. The tapered bed, unlike a conventional fluidized bed with constant cross sectional area, permits the support material 6 to expand into a reactor section with a larger cross sectional area rather than allowing the support material to escape the reactor. At higher flow rates the lower portion of the reactor is relatively free of the fluidized support material since the fluid velocity is greatly in excess of the settling velocities of the particles at that point. Simultaneously, however, a lower fluid velocity higher up the reactor results in the bed being only slightly above incipient fluidization thus preventing loss to fluidized particulate support material.

The support material utilized in the tapered column bioreactor of this invention may be any of the conventional support materials used in the prior art packed bed reactor. Such support material may be selected from the group consisting of coal particles, alumina, stainless steel, biomass particles, soil, plastics, sand, and inorganic oxides. The particle size and density of the support particles utilized in the bioreactor of this invention determine the fluid velocity which results in fluidization of the support particles. In general, however, a particle size within the range of −70 to +100 standard mesh is preferred. Particle sizes up to about 400 mesh may be used.

Virtually any type of biological catalyst which can be immobilized on a support can be used in the apparatus of this invention. This includes both self immobilized as well as chemically immobilized biocatalysts. The immobilization techniques discussed in the following articles which are herewith incorporated by reference may be utilized on the support materials of the apparatus of this invention:

Mosbach et al., *Biotechnology and Bioengineering*, Vol. XII, Pages 19–27, John Wiley & Sons, Inc. 1970;

Hicks et al., *Analytical Chemistry*, Vol. 38, No. 6, Pages 726–731, May, 1966.

Updike et al., *Nature*, Vol. 224, Pages 1122–23, Dec., 1969.

A great and unexpected advantage of the apparatus of this invention is the solution of the biomass build-up which has plagued prior art bioreactors. When microorganisms are utilized to metabolize the reactant flow through the reactor the microorganisms increase in number and volume. When operating the tapered fluidized bed of this invention biomass buildup on the support particles within the column is removed at a certain point due to the abrasive action of the fluidized bed. Alternatively, the reactant flow rate through the column may be periodically increased so as to abrade and remove excess biomass. For this reason a solid liquid separator 7 is used in conjunction with the tapered bed reactor of this invention.

The flow rates of reactants in combination with a particular tapered bed reactor may be best understood by reference to a mathmatical model which quantifies reaction conditions. Parameters may be chosen using a model which predicts bed expansion and pressure drop based upon a relatively simple summation of bed properties in a series of discrete bed volumes of the reactor. In this approach, it is assumed that the void fraction in each bed increment can be predicted by the correlation of Wen, C. Y., and Y. H. Yu, "Fluid Particle Technology,"Chem. Eng. Progr. Symp. Ser. 62, 101 (1966), which is herewith incorporated by reference.

$$\epsilon = \left[ \frac{18 N_{Re} + 2.7 N_{Re}^{1.687}}{N_{Ga}} \right]^{0.213}$$

where $\epsilon$ = bed void fraction,
$N_{Re}$ = Particle Reynolds Number,
$N_{Ga}$ = Galileo Number.

The pressure drop for each bed increment may be estimated by the force necessary to fluidize each particle, and the total pressure drop is a summation of the bed increments:

$$P = \Sigma \Delta P = \Sigma (1-\epsilon)(\rho_s - \rho_f) g \Delta Z$$

where $P, \Delta P$ = total pressure and incremental pressure drop respectively,
$\rho s, \rho f$ = solid and fluid densities,
$g$ = acceleration due to gravity,
$\Delta Z$ = incremental bed height.

The solids volume in the bed is determined by a simple material balance around each increment and total bed volume is determined by an iterative trial and error solution in which the solids volume at a candidate bed height is compared to the original solids content:

$$V_{(s)} = F_o(1-\epsilon_o) = \Sigma \Delta V (1-\epsilon)$$

where $V, \Delta V$ = total volume and incremental respectively,
$s, o$ — subscripts denoting solids and initial respectively.

This model allows the prediction of the void fraction profile, total bed volume, and total pressure drop at a variety of operating parameters.

The tapered bed biological reactor of this invention has been found to be useful for denitrifying nitrate wastes using denitrifying bacteria as the biological catalyst; for converting lactose to glucose and the conversion of lactose utilizing lactase immobilized on a porous alumina support for degrading and removing phenol from an aqueous stream utilizing T. Cutaneum as the biological catalyst; and for producing hydrogen utilizing immobilized enzymes of hydrogenase and ferredoxin.

Having generally described the apparatus of this invention the following specific examples are given as a further illustration of the utility and operation thereof.

EXAMPLE I

An aqueous solution containing phenol at a volume concentration of 750 ppm was degraded in an apparatus similar to that shown in the FIGURE of drawing. The tapered section of the column was 43 inches long having a lower opening of 1 inch diameter and expanding to an upper diameter of 3 inches. The tapered angle was 1.33° for the half angle. The column contained 300 to 500 cm³ of −30 +αstandard mesh anthracite coal. The coal particles had the commercial bacteria phenobac attached thereto to act as a biological catalyst. Phenobac is marketed by Worne Biochemicals, Inc., Westville, N.J. This bacteria is classified as a mutant strain of the genus Pseudomonas. Other equipment included a feed reservoir and feed metering pump and a settling chamber and waste reservoir. A pump was also available for recycling part of the waste stream for additional fluidization when needed. Since the reaction was aerobic, there was provisions for $O_2$ and air introduction to the bottom of the column or to a feed stream oxygenator.

The feed stream contained phenol at various concentrations listed in Table II and the trace metal additions listed in Table I. The pH was maintained within the range of 6.5 to 8.0 by the addition of $CaCl_2$. Ammonia was used as a nitrogen source and phosphate additions were made to maintain a phosphate to phenol ratio of 1:70.

Table I.

| Trace metal addition to synthetic phenol feed solutions | |
|---|---|
| Dissolved Trace Metal | Concentration ppm |
| B | 0.02 |
| Zn | .01 |
| Mo | .01 |
| Mn | .01 |
| Cu | .01 |
| Fe | .01 |

Phenol determinations down to the level of 1 ppm were performed using the 4-aminoantipyrine colorimetric method while lower levels of phenol down to 25 ppb were determined by stream distillation followed by chloroform extraction and the colorimetric method.

The tapered bed reactor was operated with approximately 2 liters of an expanded fluidized bed of anthracite particles and approximately 0.52 liter of solution above the bed prior to the column exit, a relatively narrow range of inlet flow rates of 374 to 520 milliliters per minute was used. The reactor operation was completely stable over this range and in fact it was left unattended for a period of days. In some tests air or oxygen was introduced at the bottom entry point through a porous metal frit, thus resulting in a three phase system. However, the most efficient operation was found when the feed solution was presaturated with $O_2$ and a third phase was not maintained in the reactor.

Introduction of the microorganisms into the reactor was achieved by circulating a suspension of the live microorganism through the reactor for 8 to 12 hours. This was sufficient for establishing an initial "seed" of attached microorganism that then tended to multiply rapidly reaching a steady state condition. This is the condition at which additional biomass formation does not result in additional attachment but rather in aqueous suspension. At this point the fluidized bed could be used for the continuous degradation of a waste stream, or stored at 4° C indefinitely for later use. In the latter case the bed material can be reintroduced to the bioreactor and the system will be ready for operation in a very short time.

Flow measurement was by calibrated metering pumps and/or rotameters, and aliquots of the inlet and effluent streams were collected for measurement of phenol and other constituent content.

A series of scouting tests were made in which a primary feed stream containing 450 to 4800 ppm phenol was continuously mixed with a recycle stream of the reactor effluent to make up the bioreactor feed stream. Oxygen was added either as a gas sparge (air or oxygen) to the bottom of the fluidized bed or by saturating the feed stream with $O_2$ prior to its entry to the reactor.

No attempt was made to evaluate the effect of feed stream flowrate, but there was no indication of fluid phase mass transport control of the reaction. A single bed volume was used, therefore, the effect of bed size has not yet been established.

The system was found capable of degrading phenol to levels less than 25 ppb with reactor residence times as low as a few minutes. As the phenol inlet concentration was increased in each series of test runs, a breakthrough point was reached where additional inlet phenol resulted in a significant increase in the effluent phenol concentration. With air sparging or a feed stream with $O_2$ saturation at ambient pressure, a specific conversion rate of about 6.6 grams per day per liter was observed. When the oxygen content of the system was increased by $O_2$ saturation at a pressure of 40 psig, the breakthrough conversion rate was significantly higher at about 10 grams per day per liter (Table II). Typical conversion rates in stirred tank reactors are much less than 1 gram per day per liter. A significant decrease in reactor volume is achieved with the tapered fluidized bed system.

Based on this data, the phenol conversion rate is primarily limited by available $O_2$ rather than by an inherent limitation in the biological system. Thus, at high phenol concentrations, addditional $O_2$ must be added to the system by gas sparging or overpressure, or the feed stream must be diluted by recycle of some of the reactor effluent.

The microorganism loading in the reactor was very high at about 0.1 gram dried organisms per milliliter of bed, and biomass production was typically 0.6 gram of dry microorganism per gram of phenol.

Tests were also made in which potassium thiocyanate was introduced in the feed. The bioreactor was not as efficient for thiocyanate degradation; however, a typical feed stream containing 34 ppm thiocyanate was reduced to 11 ppm.

These results from the operation of this tapered fluidized bed bioreactor for the degradation of dissolved phenolic compounds indicated that the apparatus is useful for the treatment of the aqueous waste from coal conversion processes.

Table II.

| Phenol degradation rates in tapered fluidized bed bioreactor[1] | | | | |
|---|---|---|---|---|
| Feed Stream[2] | | Effluent Phenol Concentration[3] ppm | Reactor Conversion Rate[4] g/day . liter | Oxygenation |
| Flow Rate ml/min | Phenol Concentration ppm | | | |
| 409 | 14 | 0.05 | 2.4 | Air sparge in column |
| 425 | 38 | <1 | 6.6 | Air sparge in column |
| 412 | 140 | 100 | 6.9 | Air sparge in column |
| 475 | 9 | <0.025 | 1.6 | Feed stream saturated with $O_2$ at ambient pressure |
| 480 | 17 | .050 | 3.0 | Feed stream saturated with $O_2$ at ambient pressure |
| 482 | 20 | .050 | 3.9 | Feed stream saturated with $O_2$ at ambient pressure |
| 500 | 35 | <1 | 6.6 | Feed stream saturated with $O_2$ at ambient pressure |
| 505 | 31 | 10 | 6.6 | Feed stream saturated with $O_2$ at ambient pressure |
| 374 | 30 | <.025 | 4.6 | Feed stream saturated with $O_2$ at 40 psig |
| 388 | 58 | <.050 | 9.3 | Feed stream saturated with $O_2$ at 40 psig |

Table II.-continued

| Phenol degradation rates in tapered fluidized bed bioreactor[1] | | | | |
|---|---|---|---|---|
| Feed Stream[2] | | Effluent Phenol Concentration[3] ppm | Reactor Conversion Rate[4] g/day . liter | Oxygenation |
| Flow Rate ml/min | Phenol Concentration ppm | | | |
| 391 | 63 | 0.50 | 10.2 | Feed stream saturated with $O_2$ at 40 psig |

[1]All runs were made at ambient pressure, 25±2° C, pH 7.0–7.2
[2]In all tests recycle effluent was used with a primary feed stream containing 450 to 4800 ppm phenol.
[3]Most sensitive assays less than 1 ppm had a sensitivity of 0.025 ppm. The less sensitive assay had a sensitivity of 1 ppm.
[4]Included volume of fluidized bed as well as volume of solution above the bed and volume of settling chamber.

The biological degradation of phenolic-type compounds as carried out in this example can be represented by the overall expression:

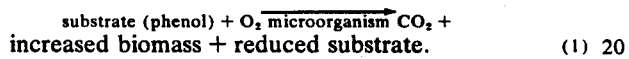
increased biomass + reduced substrate.    (1)

In this respect, the microorganism can be represented as a catalyst for the degradation. Actually the degradation process is a complex chemical pathway requiring a whole series of enzymes to catalyze various degradation steps. The proper microorganisms contain all of the necessary enzymes to achieve a rather complete breakdown. Various types of Pseudomonas bacteria are best adapted for phenol degradation. For example, one metabolic pathway determined for *Pseudomonas putida* is:

using glutaraldehyde. A slurry containing 250 grams of alumina and 500 ml of a solution off lactase in citrate-phosphate buffer in a 1 liter bottle was gently agitated for 30 minutes at room temperature. The enzyme solution was then decated (stored under refrigeration for subsequent reuse) and 500 ml of a 5% glutaraldehyde solution in citrate-phosphate buffer was added to the bottle containing the solids. The resulting slurry was then agitated for 80 minutes at room temperature. The glutaraldehyde solution was decanted and the enzyme solution previously stored was reintroduced. This was followed by another 30 minutes of agitation. The resulting catalyst was washed in buffer and was then ready for use. The system of lactase enzyme immobilized on alumina particles was used to hydrolyze lactose to glucose and galactose. The lactose chemical system was studied to determine the operating characteristics

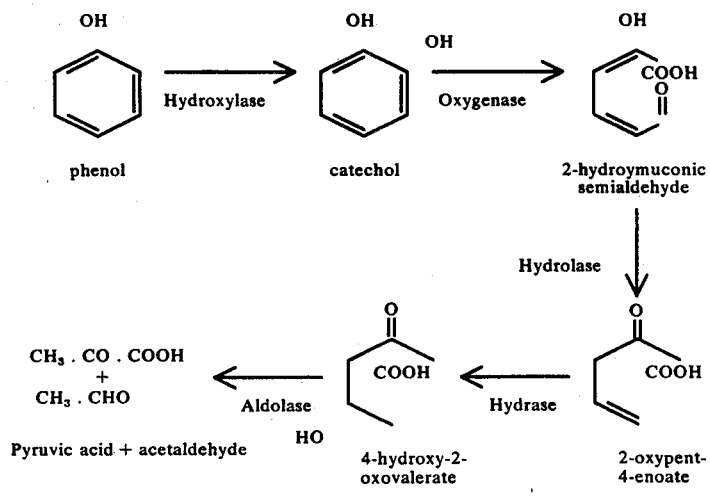

EXAMPLE II

The tapered column described in Example I was packed with 200 to 700 cm³ volume alumina at a standard mesh size within the range of −70 to +100. The enzyme lactase was attached to the alumina support of the tapered fluidized bed bioreactor and to determine its advantages compared to a conventional straight column fluidized bioreactor. The hydrolysis proceeds as follows:

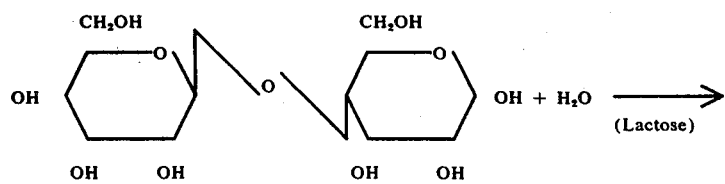

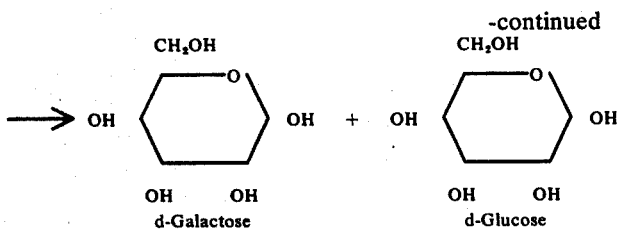

d-Galactose + d-Glucose

The lactase immobilization activity was tested using the following procedure:
A. Buffer - 0.2 M $Na_2H_2PO_4$, 0.1 m citric acid pH 3.5 (50% NaOH)
B. Wash solid in 10 V/W + buffer
C. Lactase solution: buffer plus 20 gm/L lactase
D. Mix at 37° C 10 ML of lactase solution and about 0.2 gm of immobilized enzyme of alumina for 5 minutes sample solution.
E. Assay for glucose, assuming no free enzyme in solution.

The enzyme which was immobilized had an initial activity $8 \times 10^{-5}$ moles lactase/min-gm of solid which dropped to $5.5 \times 10^{-5}$ moles lactase/min-gm solid after 3 days of use. The next 50 days of use caused only a very slight drop of activity of $5.0 \times 10^{-5}$ moles lactase/min-gm of solid.

An aqueous solution containing lactose (milk sugar) at a concentration of 50 grams per liter was passed upwardly through the column at a flow rate of 50 milliliters per minute. The lactose was converted to glucose and galactose per the above reaction. Under the above conditions conversion was found to be 90% complete when a bed of catalyst containing 700 grams of immobilized catalyzers was used.

EXAMPLE III

The tapered bioreactor of this invention can be used for the production of hydrogen from an aqueous feed stream containing a compatible reducing agent such as sodium dithionite or sodium pyruvate. This reaction is carried out by binding the enzyme hydrogenase and ferredoxin to an alumina support by sorption. The enzyme ferredoxin acts as an electron acceptor when attached to the same alumina support or dissolved in the aqueous solution. Thus, by flowing the aqueous solution containing sodium dithionite through a tapered bed bioreactor having the dimensions of 16 inches long, a lower opening of ½ inch diameter and expanding to an upper diameter of 2¾ inches, at a concentration of 3 gm/liter and at a flow rate of about 1 ml/min the following reaction occurs:

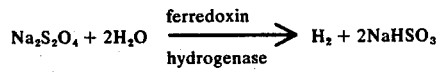

The gaseous hydrogen product is thus bubbled out of top of the reactor as the aqueous phase is removed by an overflow exit portal. The sodium bisulfite in the effluent aqueous phase can be reduced to sodium dithionite and recycled.

It is thus seen that the tapered bed biological reactor of this invention provides an apparatus which can be used for continuously carrying biologically catalyzed reactions. The apparatus itself is easily biologically activated for such applications. Many variations will be apparent to those in the art. Such variations, however, are embodied within the scope of the appended claims.

What is claimed is:

1. An apparatus for carrying out biologically catalyzed reactions, comprising:
   a vertically oriented conically-shaped column having an inlet and an outlet disposed from one another along the longitudinal axis of said column, said conically-shaped column diverging at an angle of 0.5°-2° from said axis, said inlet communicating with a section of lesser cross sectional area than said outlet;
   a particulate support material within said column; and
   a biological catalyst comprising a living microorganism attached to said particulate support.

2. The apparatus according to claim 1, including means for supplying an aqueous influent to said inlet.

3. The apparatus according to claim 2, further including means for introducing a gaseous reactant to said column.

4. The apparatus according to claim 1, wherein said support is selected from the group consisting of coal, alumina, sand, and glass.

5. The apparatus according to claim 4, wherein said support has a particle size within the range of −70 mesh to +400 standard mesh.

6. The apparatus according to claim 1, wherein said living microorganism is selected from the group of bacteria, yeasts, and algae.

7. The apparatus according to claim 1, wherein said support material comprises coal.

* * * * *